United States Patent
Moorhead

(10) Patent No.: US 10,155,922 B2
(45) Date of Patent: Dec. 18, 2018

(54) WELL PLATE

(71) Applicant: Mari Kilroy Moorhead, New York, NY (US)

(72) Inventor: Mari Kilroy Moorhead, New York, NY (US)

( * ) Notice: Subject to any disclaimer, the term of this patent is extended or adjusted under 35 U.S.C. 154(b) by 0 days.

(21) Appl. No.: 15/485,990

(22) Filed: Apr. 12, 2017

(65) Prior Publication Data

US 2017/0298313 A1    Oct. 19, 2017

Related U.S. Application Data

(60) Provisional application No. 62/323,477, filed on Apr. 15, 2016.

(51) Int. Cl.
*B01L 3/00* (2006.01)
*C12M 1/32* (2006.01)

(52) U.S. Cl.
CPC .................. *C12M 23/12* (2013.01)

(58) Field of Classification Search
CPC ............. B01L 3/5085; B01L 2300/0829
USPC ............................. 422/553, 552
See application file for complete search history.

(56) References Cited

U.S. PATENT DOCUMENTS

| | | |
|---|---|---|
| 3,545,934 A | 12/1970 | Dryden |
| 4,720,374 A | 1/1988 | Ramachandran |
| D477,416 S | 7/2003 | Roberts et al. |
| 6,602,474 B1 | 8/2003 | Tajima |
| 7,232,547 B2 | 6/2007 | Rusch et al. |
| 7,915,034 B2 | 3/2011 | Cecchi et al. |
| 8,486,692 B2 | 7/2013 | Simon |
| 8,900,851 B2 | 12/2014 | Cao |
| 2003/0143124 A1 | 7/2003 | Roberts et al. |
| 2004/0107986 A1* | 6/2004 | Neilson .................. G01K 1/18 136/204 |
| 2009/0247902 A1 | 10/2009 | Reichert et al. |
| 2009/0298116 A1 | 12/2009 | Fang et al. |
| 2011/0123415 A1 | 5/2011 | Peterson |
| 2013/0122580 A1 | 5/2013 | Tsukada et al. |
| 2015/0011012 A1 | 1/2015 | Fukuhara et al. |
| 2016/0103061 A1 | 4/2016 | Weber |

FOREIGN PATENT DOCUMENTS

| | | |
|---|---|---|
| EP | 0408280 | 7/1990 |
| EP | 2450690 A1 | 5/2012 |
| WO | WO 2014/072432 | 5/2014 |

* cited by examiner

*Primary Examiner* — Natalia Levkovich
(74) *Attorney, Agent, or Firm* — Baker & Hostetler LLP

(57) ABSTRACT

A plate includes a plate body and a well that extends into the plate body along a direction. The well extends from an opening in an upper surface of the plate to a base surface, such that the well terminates at the base surface. The well includes a tapered portion in which a cross-sectional dimension of the well that is measured in a direction perpendicular to the direction decreases as the well extends toward the base surface. The tapered portion is defined at least in part by a convex surface of an inner surface of the plate that extends between the upper surface and the base surface.

19 Claims, 3 Drawing Sheets

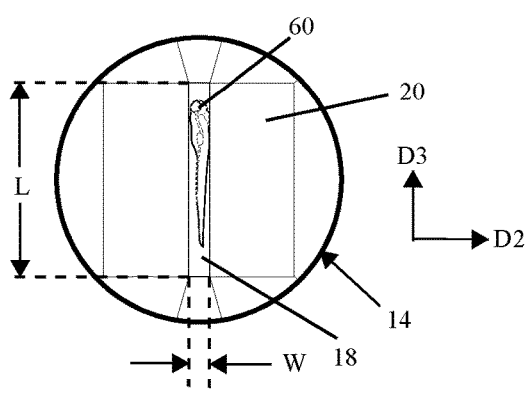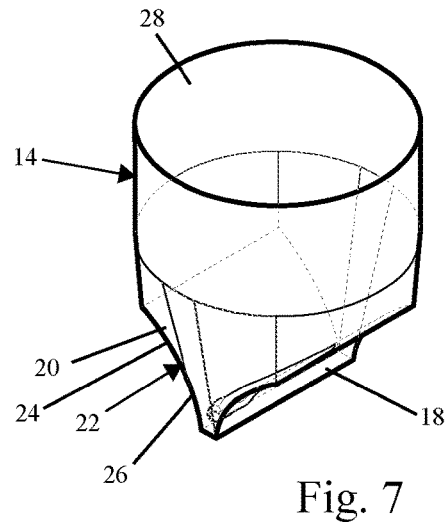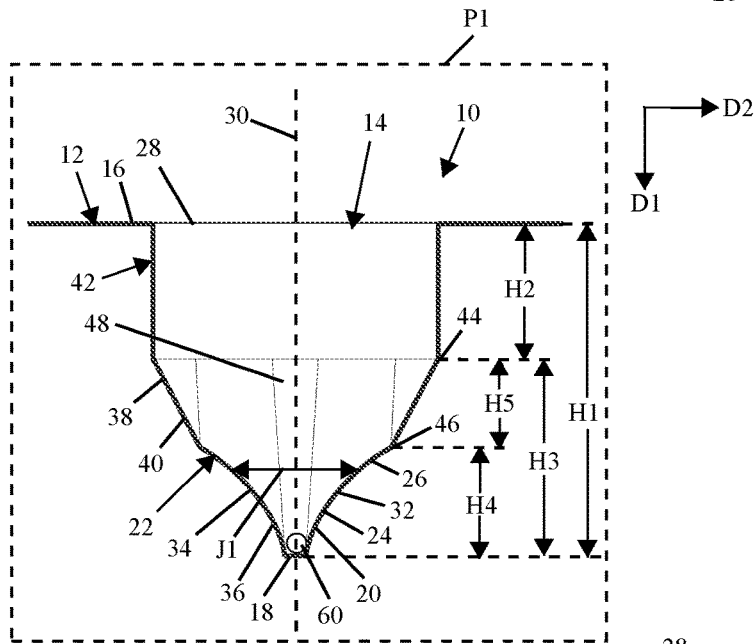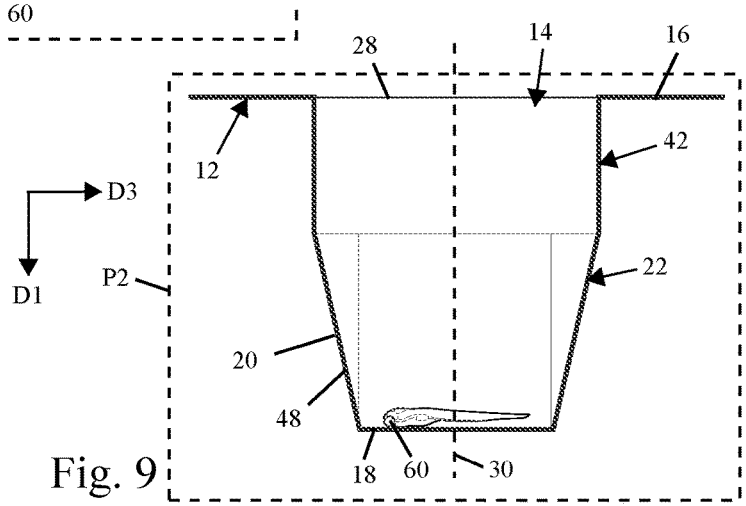

WELL PLATE

CROSS REFERENCE TO RELATED APPLICATIONS

This application claims the benefit of U.S. Provisional Application No. 62/323,477, filed Apr. 15, 2016, the disclosure of which is incorporated herein by reference in its entirety.

TECHNICAL FIELD

The present application relates generally to a plate with at least one well. More specifically, the present application relates to the structure, method of use, and method of manufacture of a plate with at least one well. The present application also relates to a process for high throughput automated imaging of specimen contained within wells of the plate.

BACKGROUND

The study of cancer in mouse avatars has recently increased in popularity as a step in the approach to treating cancer patients. According to one approach in the area of cancer research, biopsies of tumors are taken from cancer patients and then the biopsies are implanted in lines of mouse avatars. Various cancer therapy drugs can then be tested on the implanted mouse avatars to determine which of the cancer therapy drugs might be the most effective on the patient's particular tumor, and its particular pathway mutations.

However, there are drawbacks to the mouse avatar model. Patients most likely to seek the use of avatars to determine their course of cancer treatment often have a small window of expected survival time remaining, and it can take approximately 6-18 months to produce a sufficient line of mouse avatars and then obtain insightful results that could inform the course of treatment. Patients may not survive until their mouse avatars were ready to be implanted. Additionally, the cost of producing a line of mouse avatars and subsequently implanting them with biopsies of tumors from a patient is prohibitively expensive.

The use of other model organisms such as zebrafish (*Danio rerio*), provides advantages over murine avatars. For example, zebrafish embryos can be genetically modified to be transparent, enabling direct visualization of fluorescently labeled tumors in vivo from the time the tumor is implanted through migration, extravasation and invasion, as well as the formation of secondary metastases. Use of a zebrafish avatar may also result in significantly faster results in comparison to murine avatars. Additional benefits include reduced space and upkeep requirements for a relatively large number of zebrafish avatars compared to murine avatars.

One of the challenges presented by zebrafish avatars is the amount of time necessary to obtain and image the results of implanted tumors and various therapy options for treating the tumors. Accordingly, it is desirable to develop an apparatus and a method directed to patient specific testing and treatment of cancer that is more cost effective, and that requires less lead time than those used currently, such as with mouse avatars. It may be further desirable to develop an apparatus and a method to properly orient specimen such that the specimen can be visualized by a microscope accurately, with high resolution, and at a high rate of throughput.

SUMMARY

According to one embodiment, a plate comprises a plate body and a well. The plate body includes an upper surface, a base surface, and an inner surface that extends from the upper surface to the base surface. The inner surface includes a convex surface. The well extends into the plate body through the upper surface toward the base surface along a direction such that the well terminates at the base surface. The well includes a tapered portion in which a cross-sectional dimension of the well that is measured in a direction perpendicular to the direction decreases as the well extends toward the base surface. The tapered portion is defined at least in part by the convex surface.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

FIG. 6 is an isometric view of a well of the plate illustrated in FIG. 1, according to one aspect of the disclosure;

FIG. 7 is a top plan view of the well illustrated in FIG. 6;

FIG. 8 is a cross-sectional view of the well illustrated in FIG. 7, along line 8-8; and FIG. 9 is a cross-sectional view of the well illustrated in FIG. 7, along line 9-9.

DETAILED DESCRIPTION OF ILLUSTRATIVE EMBODIMENTS

Figure 1:
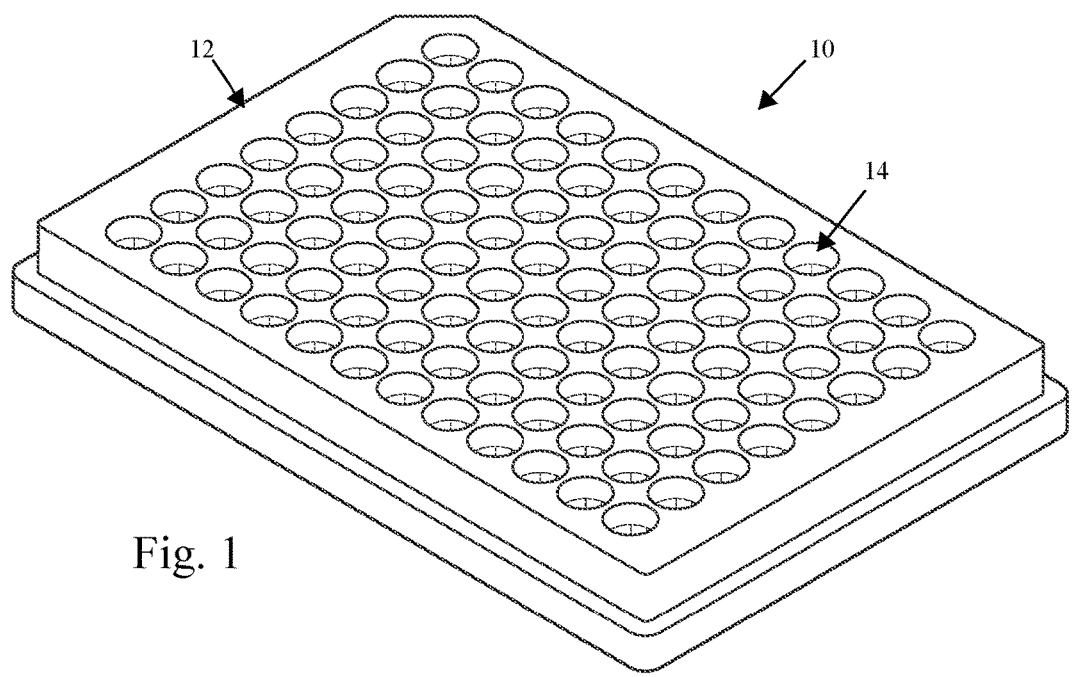
FIG. 1 is an isometric view of a plate including a plurality of wells, according to one aspect of the disclosure.

Certain terminology is used in the following description for convenience only and is not limiting. The term "aligned" as used herein in reference to two elements along a direction means a straight line that passes through one of the elements and that is parallel to the direction will also pass through the other of the two elements. The term "between" as used herein in reference to a first element being between a second element and a third element with respect to a direction means that the first element is closer to the second element as measured along the direction than the third element is to the second element as measured along the direction. The term "between" includes, but does not require that the first, second, and third elements be aligned along the direction.

Aspects of the disclosure will now be described in detail with reference to the drawings. Certain terminology is used in the following description for convenience only and is not limiting. The term "plurality", as used herein, means more than one. The terms "a portion" and "at least a portion" of a structure include the entirety of the structure. When a range of values is expressed, another embodiment includes from the one particular value and/or to the other particular value. Similarly, when values are expressed as approximations, by use of the antecedent "about," it will be understood that the particular value forms another embodiment. Further, reference to values stated in ranges includes each and every value within that range. All ranges are inclusive and combinable. Certain features of the disclosure which are described herein in the context of separate embodiments may also be provided in combination in a single embodiment. Conversely, various features of the disclosure that are described in the context of a single embodiment may also be provided separately or in any subcombination.

According to one aspect, the disclosure is configured for use in the development of a clinically viable means of using a specimen, for example zebrafish xenografts, to create avatars to model the behavior of an individual's tumor screened against a variety of anti-cancer drugs to determine potential courses of treatment. The tumor cell growth and metastasis of each avatar may be monitored to provide data relevant to the choice of courses of treatment.

According to one embodiment, zebrafish (Danio rerio) may be used as the specimen to create avatars to model the behavior of an individual's tumor. In addition, zebrafish may provide an optimal model to recapitulate human diseases, allowing the study of metastatic cell movement, microbe-host interactions, and genetic disorders due to their complex organ systems, ability to be optically transparent, and ease of culture and genetic manipulation. Zebrafish may be 80% or more accurate as human system and response models, and may also be the most cost-efficient complex model organism. As an example, a zebrafish facility configured to produce, implant, and monitor a line of zebrafish avatars may cost as little as approximately 1% of the cost of a similar facility configured to produce, implant, and monitor a line of mouse avatars.

Because the lifecycle of zebrafish is significantly shorter than that of a mouse, and because zebrafish produce more than ten times the offspring per spawning event of a mouse, zebrafish avatar assays are predicted to take significantly less time to produce results. Further benefits of zebrafish avatars compared with mouse avatars include the ability to track tumor behavior and movement through the course of drug treatment due to their transparency and faster rates of tumor growth.

Zebrafish provide a xenograft model configured to rapidly screen drugs in a personalized medicine setting. Zebrafish xenografts may be transparent which can result in a beneficial property that invasive and metastatic behavior can be directly visualized through the transparent xenograft. Preliminary studies indicate human pancreatic adenocarcinoma xenografts in zebrafish successfully demonstrate both metastatic and migration behaviors. These changing behaviors can be used as an effective evaluator for drug screening.

One of the challenges of the approach including the use of zebrafish xenograft is the amount of time necessary to obtain and image the results of the implanted tumors and various therapy options for treating the tumors. The process of analyzing the specimen and collecting the relevant data may be expedited through the use of high content imaging, robotics, efficient image processing workflow paradigm, a plate with one or more wells, or any combination thereof. Image acquisition and analysis software, for example MetaXpress, may be utilized to reduce the amount of time necessary to obtain and image the results of the implanted tumors and various therapy options for treating the tumors.

Referring to FIG. 1, a plate 10 is configured to contain one or more zebrafish avatars and enhance efficiencies related to collecting data resulting from research and experiments on the zebrafish avatars. The plate 10 includes a plate body 12 and a number of wells 14 that extend into the plate body 12. The plate 10 may include a single well 14, or a plurality of wells 14. The plurality of wells 14 may be arranged in a regular pattern of rows of wells and columns of wells. As shown in the illustrated embodiment, the plurality of wells 14 may include 96 wells arranged in eight rows and twelve columns, or eight rows of twelve wells, or an eight by twelve configuration. The plate 10 may include other numbers and arrangements, for example, an irregular arrangement of the wells 14. Each of the wells 14 is configured receive, contain, and sustain a specimen. As shown in the illustrated embodiment, each of the wells 14 is configured to receive an amount of liquid capable of sustaining a zebrafish embryo for a length of time, for example about 10 days.

Figure 2:
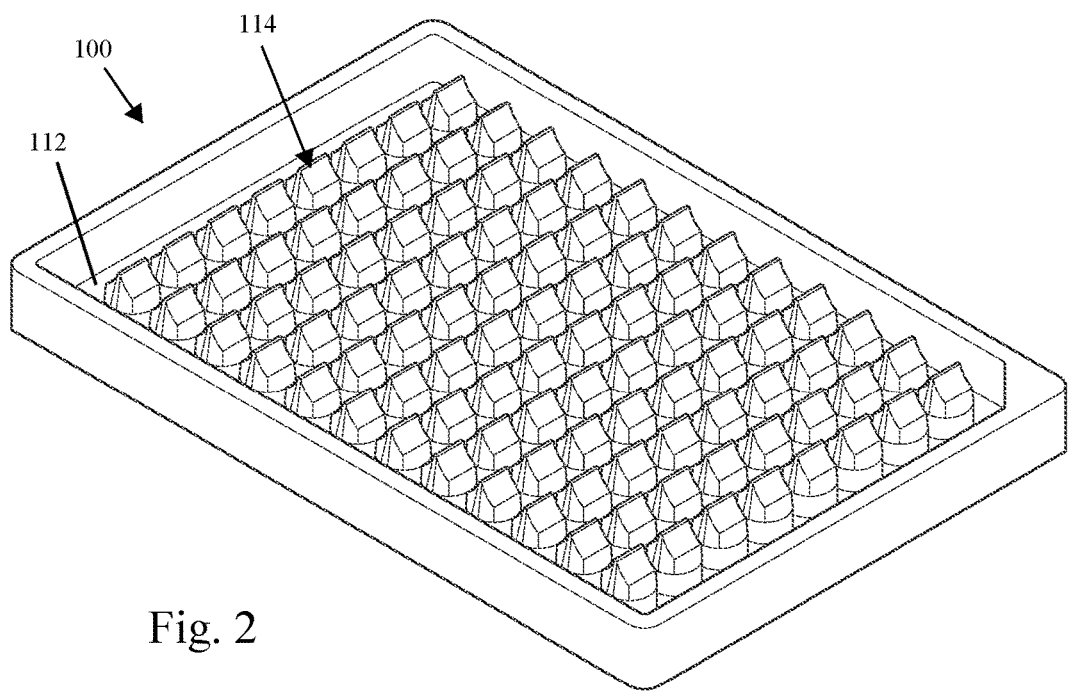
FIG. 2 is an isometric view of a mold used to manufacture the plate illustrated in FIG. 1.
Figure 3:
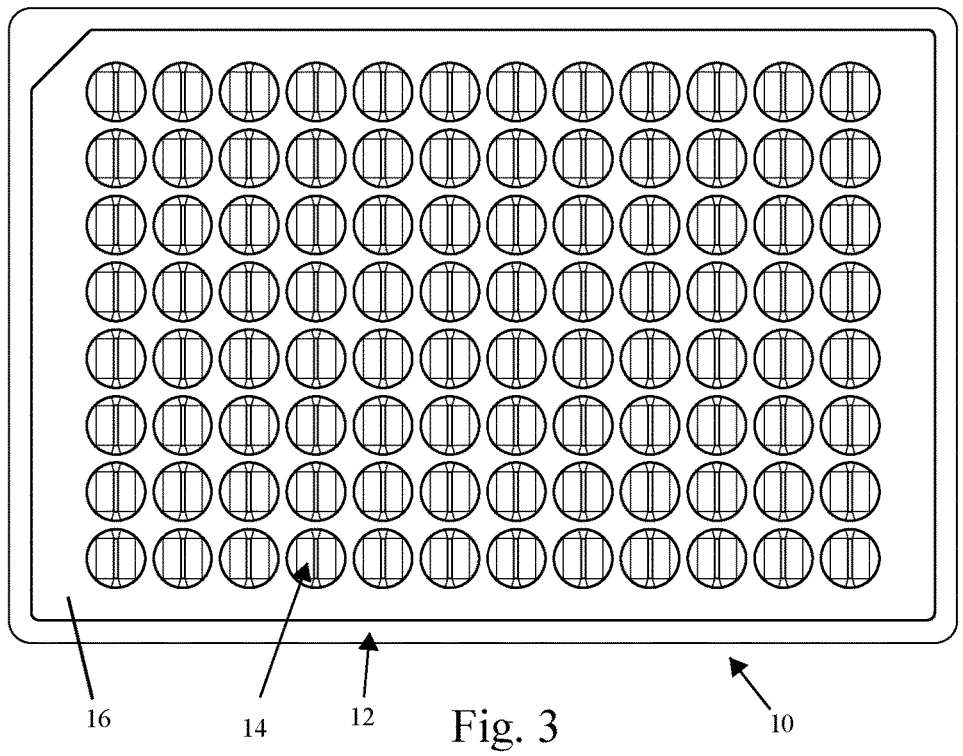
FIG. 3 is a top plan view of the plate of FIG. 1, according to one aspect of the disclosure.
Figure 4:
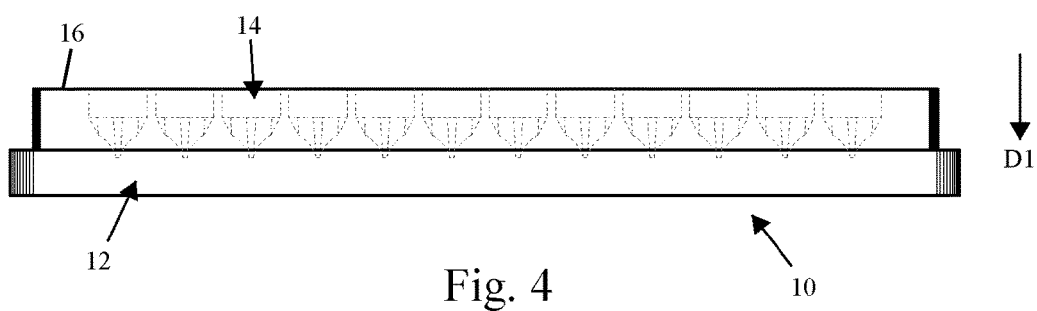
FIG. 4 is a front elevation view of the plate of FIG. 1.
Figure 5:
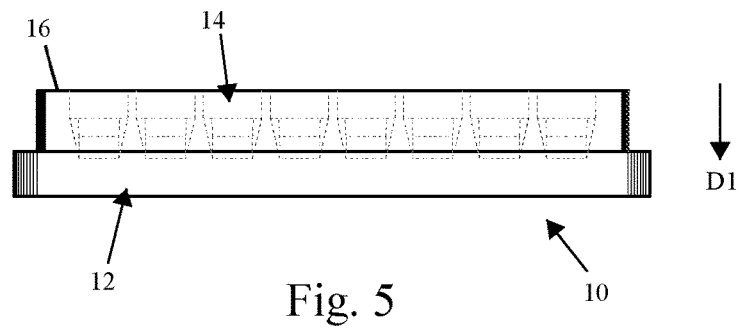
FIG. 5 is a side elevation view of the plate of FIG. 1.

Referring to FIGS. 1 and 2, according to one aspect a method of manufacturing the plate 10 includes constructing a mold 100. According to one aspect of the disclosure, the mold 100 may be manufactured through an additive manufacturing process, such as 3D printing. The mold 110 includes a lower surface 112 and a number of projections 114 that extend up from the lower surface 112. Each of the projections 114 is constructed so as to define a shape that is the inverse of the desired shape of one of the wells 14 of the plate 10. Once the mold 110 is formed, a manufacturing process, for example injection molding, is used to surround the lower surface 112 and the number of projections 114 with material. The material is allowed to cure, or harden. The mold 110 may then be removed from cured material resulting in the plate 10. According to another aspect of the disclosure, a method of manufacturing the plate includes constructing the plate directly, without the use of a mold.

Referring to FIGS. 3 to 9, the plate body 12 includes an upper surface 16, at least one base surface 18, and at least one inner surface 20. The inner surface 20 extends between the upper surface 16 and the base surface 18. According to one aspect of the disclosure, the inner surface 20 extends from the upper surface 16 to the base surface 18. The well 14 extends into the plate body 12 through the upper surface 16 toward the base surface 18 along a first direction D1, such that the well 14 terminates at the base surface 18.

The base surface 18 may be planar, perpendicular to the first direction D1, or both. According to one aspect of the disclosure, the base surface 18 defines a width W measured in a second direction D2 that is perpendicular to the first direction D1, and the base surface 18 defines a length L that is measured in a third direction D3 that is perpendicular to both the first direction D1 and the second direction D2. The plate 10 may be configured such that the length L is greater than the width W, for example at least five times greater than the width W. According to one embodiment of the disclosure, the base surface 18 defines a length L between about 3 mm and about 4 mm and a width W between about 0.5 mm and about 1 mm.

The well 14 includes a tapered portion 22 in which a cross-sectional dimension J1 of the well 14 that is measured in a direction that is perpendicular to the first direction D1, decreases as the well 14 extends toward the base surface 18. The direction perpendicular to the first direction D1 may include the second direction D2, the third direction D3, or another direction that is parallel to a plane defined by the second direction D2 and the third direction D3 cooperatively. According to one aspect of the disclosure, the inner surface 20 includes a curved surface 24, which at least partially defines the tapered portion 22. As shown in the illustrated embodiment the curved surface 24 includes a convex surface 26, which at least partially defines the tapered portion 22. According to another aspect of the disclosure, the inner surface 20 includes a linear tapered surface that is angularly offset with respect to the first direction D1, and that at least partially defines the tapered portion 22.

According to one aspect of the disclosure, the upper surface 16 defines an opening 28, and the well 14 extends into the plate body 12 through the opening 28. As shown in the illustrated embodiment, the opening 28 may be circular, and the plate 10 may define a well axis 30 that both intersects a center of the opening 28 and is parallel to the first direction D1. The well axis 30 may be a central axis that perpendicularly intersects the base surface 18, for example at a center of the base surface 18. According to another aspect of the disclosure, the opening 28 may define a non-circular shape.

The convex surface 26, according to one aspect of the disclosure, defines a convex shape that lies entirely within a first plane P1 that intersects the well axis 30, that is parallel to the first direction D1, and that intersects the convex surface 26. According to one aspect of the disclosure, the first plane P1 is parallel to the second direction D2.

According to one aspect of the disclosure, the convex surface 26 is a first convex surface 32, and the inner surface 20 includes a second convex surface 34. As shown in the illustrated embodiment, the first convex surface 32 may be positioned on one side of the well axis 30, the second convex surface 34 may be positioned on an opposite side of the well axis 30, for example such that the well axis 30 is between the first convex surface 32 and the second convex surface 34 with respect to the second direction D2. The first convex surface 32 and the second convex surface 34 taper towards one another as the first convex surface 32 and the second convex surface 34 extend toward the base surface 18.

The plate 10, according to one aspect of the disclosure, may be configured such that the tapered portion 22 includes a first tapered portion 36 and a second tapered portion 38. The plate 10 may further be configured such that the cross-sectional dimension J1 decreases at different rates in the first tapered portion 36 and the second tapered portion 38. For example, the cross-sectional dimension J1 may decrease more within the first tapered portion 36 over a given distance measured in the first direction D1, than the cross-sectional dimension decreases within the second tapered portion 38 over the same given distance. As shown in the illustrated embodiment, the convex surface 26 at least partially defines the first tapered portion 36, and the inner surface 20 includes an intermediate surface 40 that at least partially defines the second tapered portion 38 of the well 14 such that the first tapered portion 36 is positioned closer to the base surface 18 with respect to the first direction D1 than the second tapered portion 38 is positioned to the base surface 18 with respect to the first direction D1.

The convex surface 26 defines a first radius of curvature that lies entirely within the first plane P1. The intermediate surface 40, according to one aspect of the disclosure, defines a second radius of curvature that lies entirely within the first plane P1. As shown in the illustrated embodiment, the second radius of curvature may be larger than the first radius of curvature. Alternatively, the first radius of curvature may be larger than the second radius of curvature. According to another aspect of the disclosure, the intermediate surface 40 may be planar such that the intermediate surface 40 defines a straight line segment that that lies entirely within a plane, for example the first plane P1, that intersects the well axis 30, that is parallel to the first direction D1, and that intersects the intermediate surface 40.

According to one aspect of the disclosure, the well 14 may include a non-tapered portion 42 in which the cross-sectional dimension J1 remains constant as the well 14 extends toward the base surface 18. The non-tapered portion 42 is defined by the inner surface 20, and the non-tapered portion 42 may be positioned closer to the upper surface 16 with respect to the first direction D1 than the tapered portion 22 is to the upper surface 16 with respect to the first direction D1. The plate 10 may be configured such that the second tapered portion 38 is between the non-tapered portion 42 and the first tapered portion 36 with respect to the first direction D1.

The well 14 defines a first height H1 measured from the opening 28 to the base surface 18 in the first direction D1. The well 14 may further define a second height H2, a third height H3, a fourth height H4, a fifth height H5, or any combination thereof. The second height H2 is measured along the first direction D1 from the opening 28 to an intersection 44 of the tapered portion 22 and the non-tapered portion 42. The third height H3 is measured along the first direction D1 from the intersection 44 to the base surface 18. The fourth height H4 is measured along the first direction D1 from an intersection 46 of the first tapered portion 36 and the second tapered portion 38 to the base surface 18. The fifth height H5 is measured along the first direction D1 from the intersection 44 to the intersection 46. According to one aspect of the disclosure, the third height H3 is greater than the second height H2, as shown in the illustrated embodiment. Alternatively, the plate 10 may be configured such that the second height H2 is greater than the third height H3. According to one aspect of the disclosure, the fourth height H4 is greater than the fifth height H5, as shown in the illustrated embodiment. Alternatively, the plate 10 may be configured such that the fifth height H5 is greater than the fourth height H4.

The inner surface 20 may include a third surface 48 that is radially offset from both the convex surface 26 and the intermediate surface 40 with respect to the well axis 30. As shown in the illustrated embodiment, a portion of the third surface 48 may be radially offset from both a portion of the convex surface 26 and a portion of the intermediate surface 40 by about 90 degrees. The third surface 48, as shown, may define a portion of both the first tapered portion 36 and the second tapered portion 38. According to one aspect of the disclosure, the third surface 48 defines a straight line segment that that lies within a second plane P2 that intersects the well axis 30, that is parallel to the first direction D1, and that intersects the third surface 48. The second plane P2 may be perpendicular to the first plane P1. According to another aspect of the disclosure, the third surface 48 is configured so as to define a radius of curvature that lies entirely within the second plane P2. The radius of curvature of the third surface 48 may be constant along the first direction D1, or may vary along the first direction D1.

In use, the plate 10 is configured to sustain a specimen over a length of time. A specimen 60, for example a zebrafish embryo, is implanted with a sample, for example a tumor. One or more of the wells 14 of the plate 10 is filled with a liquid capable of sustaining the specimen 60. The liquid may include a saline balanced water solution. The liquid may also include an agent, for example an anti-cancer agent. The specimen 60 is placed in the liquid filled well 14. A plurality of the specimen 60 may be placed, such that one specimen 60 is placed in each of the plurality of liquid filled wells 14. The steps in this paragraph may be repeated for the desired number of specimen 60. For example, a plate 10 with ninety-six wells 14 may have ninety-six specimen 60 contained within the wells 14, one specimen 60 in each well 14.

An agent, such as a sedative, may be added to the liquid filled well 14 with the specimen 60 inside. The sedative may be added to the wells 14 through the use of an automated liquid handling system that is configured to quickly and accurately dispense an equal amount of sedative into each of the wells 14. The sedative causes the specimen 60 to sink towards the base surface 18. The shape of the inner surface 20 is configured to guide the sinking specimen 60 toward the base surface 18 and align the specimen 60 with the base surface 18. According to one aspect of the disclosure, the aligned specimen 60 rests entirely on the base surface 18, as shown in FIGS. 6 and 7, and is not resting with a significant portion of the specimen 60 on the inner surface 20. Thus, the shape of the inner surface 20, for example the convex surface 26, may be further configured to minimize or prevent the sinking specimen 60 from coming to rest such that the specimen 60 is supported by the inner surface 20. The steps in this paragraph may be repeated for the desired number of specimen 60 in a corresponding number of the wells 14.

Aligning the specimen 60 with the base surface as described above, allows the location of the specimen 60 to be reliably predicted within the well 14. The predictability of the location enables high-speed and high-accuracy data collection of the sample within the specimen 60. For example an automated high-throughput, high-content imaging system that may include a camera, a microscope, or both may be used to collect and record data related to the specimen 60. The high-throughput, high-content imaging system may be configured to move components of the system, for example the camera, the microscope, or both, move the plate 10, or move both the plate 10 and components of the system to align the specimen 60 within each well 14 of the plate 10 with components of the system and record data. A plate with a well not configured as the plate 10 and the well 14 as described herein may result in less predictability of the location of the sedated specimen 60, and this reduced predictability may result in data collection that is slower, less accurate, or both.

The method of use may include the step of removing the liquid that contains the sedative from each of the wells 14. The step of removing the liquid may be performed after the data collection step. The step of removing the liquid may be performed through the use of an automated liquid handling system. The method of use may further include the step of refilling each of the wells 14 with replacement liquid that does not contain the sedative. After the data collection step, the plate 10 may be stored for a desired amount of time to allow development of the sample, or treatment of the sample with an agent, such as an anti-cancer drug, before performing the sedating and data collecting steps again.

Thus, a proposed individualized cancer treatment may include a number of steps described below. The first step includes obtaining a biopsy tumor from a patient and then either directly implanting portions of the biopsied tumor into a plurality of specimen, for example a plurality of zebrafish avatars. Alternatively or in addition to the step of directly implanting, portions of the biopsied tumor may be cultured. The second step includes arraying and testing a plurality of the specimen using a variety of potential treatment options. The third step includes recording and analyzing data generated during the second step. For example, the effect of a plurality of drugs on the growth and metastasis of the implanted tumors may be scored microscopically. From the data the best courses of treatment may be determined for the patient based on their tumor's specific properties, for example mutated signaling pathways.

Properly orienting the plurality of specimen by hand such that the specimen can be visualized by a microscope both accurately and at a high rate of throughput may be time consuming. Current methods include manually orienting each embryo, orienting in viscous media such as agar, or using molded agar plates to hold the fish in place. Efficiency of the imaging and analysis processes may be increased by utilizing high throughput image screening (HTPS), for example the ImageXpress Micro-Confocal high content imaging (HCI) system, which has the ability to auto-focus and capture throughput of over 160,000 wells per day.

However, HTPS and HCI systems are designed for cell cultures and fixed organisms rather than live model organisms. Reliably positioning a live specimen or a plurality of live specimen such that the HTPS and HCI systems can image and analyze the specimen may be accomplished with the use of the plate 10 as described herein.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

What is claimed:

1. A plate comprising:
    a plate body including an upper surface, a base surface, and an inner surface that extends from the upper surface to the base surface, the inner surface including a convex surface; and
    a well at least partially defined by the inner surface such that the well extends into the plate body through the upper surface and toward the base surface along a first direction that is perpendicular to the upper surface, the well terminating at the base surface, and the well including a tapered portion in which a cross-sectional dimension of the well that is measured in a second direction that is perpendicular to the first direction decreases as the well extends toward the base surface,
    wherein the tapered portion is defined at least in part by the convex surface, the tapered portion includes a first tapered portion and a second tapered portion, the convex surface at least partially defines the first tapered portion, the inner surface includes an intermediate surface that at least partially defines the second tapered portion of the well, and the first tapered portion is positioned closer to the base surface with respect to the first direction than the second tapered portion is positioned to the base surface with respect to the first direction.

2. The plate of claim 1, wherein the base surface is planar and perpendicular to the first direction.

3. The plate of claim 2, wherein the base surface defines a width measured in the second direction, and the base surface defines a length that is measured in a third direction that is perpendicular to both the first direction and the second direction.

4. The plate of claim 3, wherein the length is greater than the width.

5. The plate of claim 4, wherein the length is at least five times greater than the width.

6. The plate of claim 3, wherein the upper surface defines a circular opening, and the well extends into the plate body through the circular opening along a well axis that both intersects a center of the circular opening and is parallel to the first direction.

7. The plate of claim 1, wherein the upper surface defines a circular opening, and the well extends into the plate body through the circular opening along a well axis that both intersects a center of the circular opening and is parallel to the first direction.

8. The plate of claim 7, wherein the convex surface defines a convex shape within a plane that: 1) intersects the well axis; 2) is parallel to the first direction; and 3) intersects the convex surface.

9. The plate of claim 7, wherein the convex surface is a first convex surface, the first convex surface is positioned on one side of the well axis, the inner surface includes a second convex surface that is positioned on an opposite side of the well axis, and the first convex surface and the second convex surface taper towards one another as the first convex surface and the second convex surface extend toward the base surface.

10. The plate of claim 1, wherein the well includes a non-tapered portion defined by the inner surface, such that a cross-sectional dimension of the non-tapered portion of the well remains constant as the well extends toward the base surface.

11. The plate of claim 10, wherein the non-tapered portion is positioned closer to the upper surface with respect to the first direction than the first tapered portion is positioned to the upper surface with respect to the first direction, and the second tapered portion is between the non-tapered portion and the first tapered portion with respect to the first direction.

12. The plate of claim 10, wherein the well includes a first height measured along the first direction from the upper surface to an intersection of the tapered portion and the non-tapered portion, the well defines a second height measured along the first direction from the intersection to the base surface, and the second height is greater than the first height.

13. The plate of claim 1, wherein the convex surface defines a first radius of curvature that lies within a plane that: 1) intersects the well axis; 2) is parallel to the direction; and 3) intersects the convex surface, the intermediate surface defines a second radius of curvature that lies within the plane, and the second radius of curvature is larger than the first radius of curvature.

14. The plate of claim 1, wherein the intermediate surface is planar and defines a straight line segment that that lies within a plane that: 1) intersects the well axis; 2) is parallel to the first direction; and 3) intersects the intermediate surface.

15. The plate of claim 1, wherein the upper surface defines a circular opening, the well extends into the plate body through the circular opening along a well axis that both intersects a center of the circular opening and is parallel to the first direction.

16. The plate of claim 15, wherein the convex surface is a first surface, the intermediate surface is a second surface, the inner surface includes a third surface, the third surface is radially offset from the first surface and the second surface with respect to the well axis, and the third surface defines a portion of both the first tapered portion and the second tapered portion.

17. The plate of claim 16, wherein the third surface defines a straight line segment that that lies within a plane that: 1) intersects the well axis; 2) is parallel to the first direction; and 3) intersects the third surface.

18. The plate of claim 16, wherein the third surface defines a radius of curvature that that lies within a plane that: 1) intersects the well axis;2) is parallel to the first direction; and 3) intersects the third surface.

19. The plate of claim 18, wherein the radius of curvature is constant.

* * * * *

UNITED STATES PATENT AND TRADEMARK OFFICE
CERTIFICATE OF CORRECTION

PATENT NO. : 10,155,922 B2
APPLICATION NO. : 15/485990
DATED : December 18, 2018
INVENTOR(S) : Mari Kilroy Moorhead Page 1 of 1

It is certified that error appears in the above-identified patent and that said Letters Patent is hereby corrected as shown below:

On the Title Page

Please insert --(73) Assignee: The Moorhead Group, New York, New York (US)--

Signed and Sealed this
Twenty-third Day of July, 2019

Andrei Iancu
*Director of the United States Patent and Trademark Office*